(12) United States Patent
Achhanath et al.

(10) Patent No.: US 8,946,483 B2
(45) Date of Patent: Feb. 3, 2015

(54) PRECURSOR COMPOUNDS AND METHODS FOR MAKING SAME

(75) Inventors: Radha Achhanath, Karnataka (IN); Srinath Balaji, Karnataka (IN); Asfal Mohammed Kadavilpparampu Mohamed, Bangalore (IN); Sondre Nilsen, Olso (NO); Steven Michael Fairway, Oslo (NO)

(73) Assignee: GE Healthcare Limited, Buckinghamshire (GB)

( * ) Notice: Subject to any disclaimer, the term of this patent is extended or adjusted under 35 U.S.C. 154(b) by 0 days.

(21) Appl. No.: 14/131,442

(22) PCT Filed: Jul. 20, 2012

(86) PCT No.: PCT/EP2012/064254
§ 371 (c)(1),
(2), (4) Date: Jan. 8, 2014

(87) PCT Pub. No.: WO2013/011115
PCT Pub. Date: Jan. 24, 2013

(65) Prior Publication Data
US 2014/0135531 A1    May 15, 2014

Related U.S. Application Data

(60) Provisional application No. 61/565,534, filed on Dec. 1, 2011.

(30) Foreign Application Priority Data

Jul. 21, 2011    (IN) .......................... 2050/DEL/2011
Nov. 23, 2011   (GB) .................................. 1120225.6

(51) Int. Cl.
| C07C 43/20 | (2006.01) |
| C07C 45/00 | (2006.01) |
| C07C 41/00 | (2006.01) |
| C07C 45/78 | (2006.01) |
| C07C 41/44 | (2006.01) |
| C07C 43/174 | (2006.01) |
| C07C 45/42 | (2006.01) |
| C07C 49/757 | (2006.01) |
| C07C 319/20 | (2006.01) |

(52) U.S. Cl.
CPC ................. *C07C 45/78* (2013.01); *C07C 41/44* (2013.01); *C07C 43/174* (2013.01); *C07C 45/42* (2013.01); *C07C 49/757* (2013.01); *C07C 319/20* (2013.01); *C07C 2101/04* (2013.01)
USPC ........... 568/322; 568/323; 568/324; 568/626; 568/663

(58) Field of Classification Search
USPC .......................... 568/322, 323, 324, 626, 663
See application file for complete search history.

(56) References Cited

U.S. PATENT DOCUMENTS

2006/0292073 A1    12/2006    Goodman

FOREIGN PATENT DOCUMENTS

| EP | 0454270 | 4/1991 |
| WO | 2007/001958 | 1/2007 |
| WO | 2007/061670 | 5/2007 |

OTHER PUBLICATIONS

Avram, Chemische Berichte, vol. 90, Jan 1, 1957, pp. 1424-1431.
Michel Tetrahedron, vol. 56, No. 24, June 16, 2000, pp. 4253-4260.
Tanner, Canadian Journal of Chemistry, vol. 54, No. 15, Aug. 1, 1976, pp. 2417-2425.
O'Hooghe, The Journal of Organic Chemistry, vol. 69, No. 8, Apr. 1, 2004, pp. 2703-2710.
PCT/EP2012/064254 ISRWO Dated Nov. 15,2002.
GB1120225.6 Search Report Dated May 10, 2012.

*Primary Examiner* — Sikarl Witherspoon

(57) ABSTRACT

The present invention relates to a method of obtaining radiopharmaceutical precursors, and in particular precursors to protected amino acid derivatives, which are used as precursors for production of radiolabelled amino acids for use in in vivo imaging procedures, such as positron emission tomography (PET).

21 Claims, No Drawings

PRECURSOR COMPOUNDS AND METHODS FOR MAKING SAME

This application is a filing under 35 U.S.C. 371 of international application number PCT/EP2012/064254, filed Jul. 20, 2012, which claims priority to India application number 2050/DEL/2011 filed Jul. 21, 2011 and Great Britain application number 1120225.6 filed Nov. 23, 2011 and U.S. application 61/565,534 filed Dec. 1, 2011, the entire disclosure of which is hereby incorporated by reference.

FIELD OF THE INVENTION

The present invention relates to a method of obtaining radiopharmaceutical precursors, and in particular precursors to protected amino acid derivatives, which are used as precursors for production of radiolabelled amino acids for use in in vivo imaging procedures, such as positron emission tomography (PET).

BACKGROUND

In recent years, a series of radioactive halogen-labeled amino acid compounds including [$^{18}$F]-1-amino-3-fluorocyclobutanecarboxylic acid ([$^{18}$F]-FACBC) have been designed as novel radiopharmaceuticals. [$^{18}$F]-FACBC is considered to be effective as a diagnostic agent for highly proliferative tumors, because it has a property of being taken up specifically by amino acid transporters on the tumors.

Though there are a number of published approaches for the synthesis of [$^{18}$F]-FACBC and its precursors, some suffer from being lengthy (e.g., EP1978015), low yields or from problems associated with the purification of either the final product (i.e., [$^{18}$F]-FACBC) and/or the intermediates leading to the production of the product. Accordingly, there remains a need for new methods for the production of [$^{18}$F]-FACBC and/or intermediates leading to the production of [$^{18}$F]-FACBC.

SUMMARY OF THE INVENTION

In one embodiment, the invention relates to a method for substantially removing a 1,2-dihalogen impurity from a product mixture comprising:
(a) reacting the product mixture with an alkoxide, thereby transforming the 1,2-dihalogen impurity into an alkene; and
(b) removing the alkene.

In some embodiments, the alkoxide is methoxide (e.g., sodium methoxide). In some embodiments, the alkene is removed by vacuum (e.g., vacuum distillation).

In other embodiments, the invention relates to a method for substantially removing a 1,2-dihalogen impurity of the formula (I)

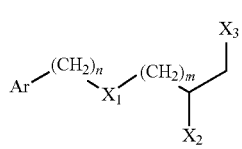

wherein:
Ar is a substituted or unsubstituted aryl or substituted or unsubstituted heteroaryl group;
$X_1$ is a heteroatom;
$X_2$ and $X_3$ are, independently the same or different, halogen; and
m and n are, independently the same or different, an integer from 1 to 5;
from a product mixture comprising a compound of the formula (II)

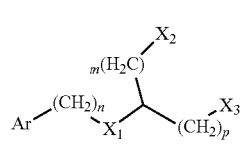

wherein Ar, $X_1$, $X_2$, $X_3$, n, and m are as defined above and p is an integer from 1 to 5;
wherein the method comprises:
(a) reacting the product mixture with an alkoxide, thereby transforming the 1,2-dihalogen impurity of the formula (I) into an alkene of the formula (III)

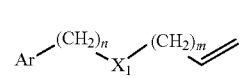

wherein Ar, $X_1$, n, and m are as defined above; and
(b) removing the alkene of formula (III).

In some embodiments, the alkoxide is methoxide (e.g., sodium methoxide). In some embodiments, the alkene of formula (III) is removed by vacuum (e.g., vacuum distillation). In other embodiments, m and n in the compound of formula (I) are 1. In still other embodiments, m and n in the compound of formula (II) are 1. In yet other embodiments, m and n in the compound of formula (III) are 1. In other embodiments, $X_1$ is oxygen. In other embodiments, $X_2$ and/or $X_3$ are bromine. In one embodiment both $X_2$ and $X_3$ are bromine. In still other embodiments, Ar is phenyl.

In some embodiments, the compound of formula (I) is a compound of the formula (IV):

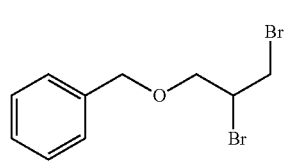

In some embodiments, the compound of formula (II) is a compound of the formula (V):

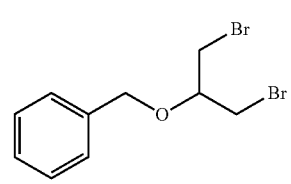

In some embodiments, the compound of formula (III) is a compound of the formula (VI):

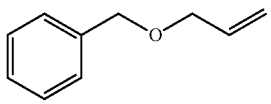
(VI)

In still other embodiments, the invention relates to a method of making a compound of the formula (VIII):

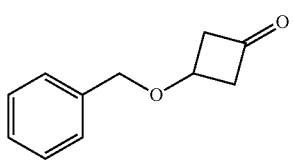
(VIII)

the method comprising:
(a) reacting benzyl bromide with epibromohydrin to give a product mixture comprising a compound of the formula (IV) and a compound of the formula (V):

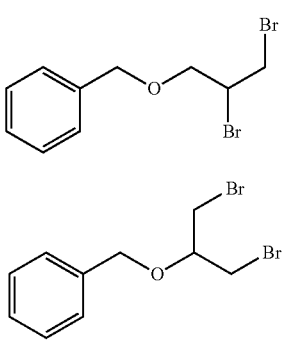
(IV)

(V)

(b) reacting the product mixture with an alkoxide, thereby transforming the compound of formula (IV) into a compound of the formula (VI):

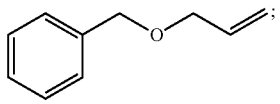
(VI)

(c) removing the compound of formula (VI) such that the compound of formula (V) remains;
(d) reacting the remaining compound of formula (V) with methanesulfinyl-methylsulfanyl-methane to give a compound of the formula (VII):

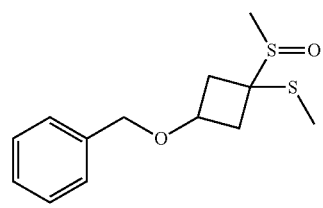
(VII)

and performing a work-up of the reaction with toluene;

(e) hydrolyzing the compound of formula (VII) in toluene to give a compound of the formula (VIII); and
(f) purifying the compound of formula (VIII).
In some embodiments, said purifying comprises vacuum distillation.

DETAILED DESCRIPTION

In some embodiments, the invention relates to a method for substantially removing a 1,2-dihalogen impurity from a product mixture comprising:
(a) reacting the product mixture with an alkoxide, thereby transforming the 1,2-dihalogen impurity into an alkene; and
(b) removing the alkene.

As used herein, the term "halogen" or "halo," used alone or in combination, refers to fluorine, chlorine, bromine or iodine.

As used herein, the term "alkoxide" means alkyl-O—$X^+$, wherein $X^+$ is a counterion. Exemplary counterions include lithium, sodium, potassium, cesium and the like. In some embodiments, the counterion is sodium. Exemplary sodium alkoxides include sodium methoxide, sodium ethoxide, sodium propoxide, sodium t-butoxide, and the like. In a preferred embodiment, the alkoxide is methoxide. In some embodiments, the preferred alkoxide is sodium methoxide.

As used herein, "alkyl" means carbon chains which may be linear or branched or combinations thereof. Examples of alkyl groups include methyl, ethyl, propyl, isopropyl, butyl, sec- and tert-butyl, pentyl, hexyl, heptyl and the like. Preferred alkyl groups are $C_{1-10}$ alkyl groups, e.g., $C_{1-5}$ alkyl and $C_{1-3}$ alkyl.

As used herein, the term "alkene" or "alkenyl" refers to carbon chains containing at least one unsaturated carbon-carbon bond. The carbon chains may be linear, branched or combinations thereof. In some embodiments, the alkene is a $C_{2-10}$ alkene, e.g., a $C_{2-5}$ alkene or a $C_{2-3}$ alkene. In some embodiments, the alkene can comprise one or more heteroatoms. As used herein, the term "heteroatom" refers to the atoms N, O, P, B, S, and Si. In some embodiments the hetero atom is selected from N, O and S.

In some embodiments, the alkene has a sufficiently different physical or chemical property that allows it to be separated from the product mixture. Thus, for example, the alkene can be a low-boiling alkene that can be removed by applying a vacuum; by distillation; or by employing vacuum distillation. Alternatively, the alkene can have a sufficiently different $R_f$ (i.e. retardation factor) thus allowing for its separation and removal by employing chromatographic methods (e.g., HPLC, column chromatography, and the like). In still another alternative, the alkene, due to the presence of the double bond and its inherent reactivity, could be converted selectively (i.e., without affecting the desired product in the product mixture) chemically into another product that can be removed by methods known in the art.

In addition, the alkene may be substituted or unsubstituted. When the alkene is substituted, the substituent can be a $C_{5-10}$ aromatic group or any suitable substituents known in the art, including halo groups, perfluoroalkyl groups, perfluoroalkoxy groups, alkyl groups, alkenyl groups, alkynyl groups, hydroxy groups, alkoxy groups, aryl or heteroaryl groups, aryloxy or heteroaryloxy groups, aralkyl or heteroaralkyl groups, aralkoxy or heteroaralkoxy groups, amino groups and the like, or combinations thereof. In some embodiments, the $C_{5-10}$ aromatic group that can be present on the alkene is, itself, substituted by any of the aforementioned substituents.

As used herein, "alkynyl" and other like terms include carbon chains containing at least one carbon-carbon triple bond.

As used herein, "alkoxy" means alkyl-O—, wherein "alkyl" is defined above.

The term "aryl" means an aromatic substituent that is a single ring or multiple rings fused together. Aryl groups encompass $C_{2-10}$ aromatic groups. Exemplary aryl groups include, without limitation, phenyl, naphthyl, anthracenyl, pyridinyl, pyrazinyl, pyrimidinyl, triazinyl, thiophenyl, furanyl, pyrrolyl, oxazolyl, imidazolyl, triazyolyl, and tetrazolyl groups. Aryl groups that contain one or more heteroatoms (e.g., pyridinyl) are often referred to as "heteroaryl groups." When formed of multiple rings, at least one of the constituent rings is aromatic. In some embodiments, at least one of the multiple rings comprise a heteroatom, thereby forming hetero atom-containing aryl groups.

The terms "aryloxy" and "heteroaryloxy," as used herein, mean aryl-O— and heteroaryl-O—, respectively.

The terms "aralkyl" and "heteroaralky" as used herein, mean an aryl or heteroaryl group bonded to an alkyl group, respectively.

The term "arylalkoxy" and "heteroaryloxy," as used herein, means an aryl or heteroaryl group bonded to an alkoxy group.

As used herein, the term "amino" means the group —NRR', wherein R and R' are, independently, hydrogen, alkyl or aryl, where the alkyl and aryl groups are optionally substituted.

In another embodiment, the invention relates to a method for substantially removing a 1,2-dihalogen impurity of the formula (I):

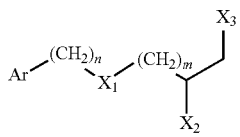

wherein:
Ar is a substituted or unsubstituted aryl or substituted or unsubstituted heteroaryl group;
$X_1$ is a heteroatom;
$X_2$ and $X_3$ are, independently the same or different, halogen; and
m and n are, independently the same or different, an integer from 1 to 5;
from a product mixture comprising a compound of the formula (II)

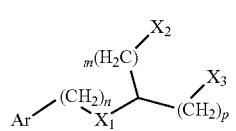

wherein Ar, $X_1$, $X_2$, $X_3$, n, and m are as defined above and p is an integer from 1 to 5;
wherein the method comprises:
(a) reacting the product mixture with an alkoxide, thereby transforming the 1,2-dihalogen impurity of the formula (I) into an alkene of the formula (III)

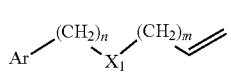

wherein Ar, $X_1$, n, and m are as defined above; and
(b) removing the alkene of formula (III).

In some embodiments, the alkene of formula (III) is removed by vacuum (e.g., vacuum distillation).

In some embodiments, the compound of the formula (II) is a compound where m, n, and p are 1. In certain other embodiments, the compound of the formula (II) is a compound where m, n, and p are 1; and $X_1$ is oxygen. In still other embodiments, the compound of the formula (II) is a compound where m, n, and p are 1; $X_1$ is oxygen; and $X_2$ and/or $X_3$ are bromine. In yet other embodiments, the compound of the formula (II) is a compound where m, n, and p are 1; $X_1$ is oxygen; and $X_2$ and $X_3$ are bromine. In other embodiments, the compound of the formula (II) is a compound where Ar is phenyl; m and n are 1; $X_1$ is oxygen; and $X_2$ and $X_3$ are bromine, such that the compound of the formula (II) is a compound of the formula (V):

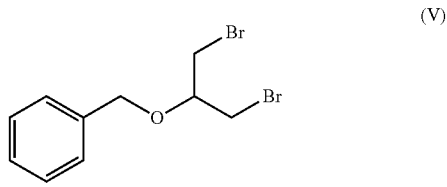 [SMILES: BrCC(CBr)OCc1ccccc1]

In some embodiments, the 1,2-dihalogen impurity of the formula (I) is a compound where m and n are 1. In certain other embodiments, the 1,2-dihalogen impurity of the formula (I) is a compound where m and n are 1; and $X_1$ is oxygen. In still other embodiments, the 1,2-dihalogen impurity of the formula (I) is a compound where m and n are 1; $X_1$ is oxygen; and $X_2$ and/or $X_3$ are bromine. In yet other embodiments, the 1,2-dihalogen impurity of the formula (I) is a compound where m and n are 1; $X_1$ is oxygen; and $X_2$ and $X_3$ are bromine. In other embodiments, the 1,2-dihalogen impurity of the formula (I) is a compound where Ar is phenyl; m and n are 1; $X_1$ is oxygen; and $X_2$ and $X_3$ are bromine, such that the 1,2-dihalogen impurity of the formula (I) is a compound of the formula (IV):

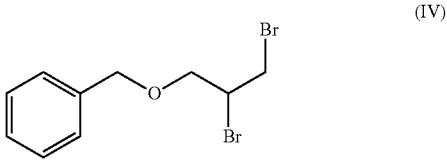 [SMILES: BrCC(Br)COCc1ccccc1]

In some embodiments, the compound of the formula (III) is a compound where m and n are 1. In certain other embodiments, the compound of the formula (III) is a compound where m and n are 1; and $X_1$ is oxygen. In other embodiments, the compound of the formula (I) is a compound where Ar is phenyl; m and n are 1; and $X_1$ is oxygen such that the compound of the formula (III) is a compound of the formula (VI):

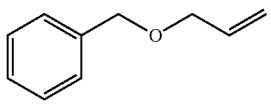

(VI)

In describing and claiming the present invention, the following terminology will be used in accordance with the additional definitions set forth below.

The singular forms "a," "an," and, "the" include plural referents unless the context clearly dictates otherwise. Thus, for example, reference to "an alkoxide" includes reference to one or more alkoxides.

As used herein, the term "substantially" refers to the complete or nearly complete extent or degree of an action, characteristic, property, state, structure, item, or result. For example, an object that is "substantially" enclosed would mean that the object is either completely enclosed or nearly completely enclosed. The exact allowable degree of deviation from absolute completeness may in some cases depend on the specific context. However, generally speaking the nearness of completion will be so as to have the same overall result as if absolute and total completion were obtained. The use of "substantially" is equally applicable when used in a negative connotation to refer to the complete or near complete lack of an action, characteristic, property, state, structure, item, or result. For example, "substantially removing a 1,2-dihalogen impurity" means either completely removing, or so nearly completely removing the 1,2-dihalogen impurity that the effect would be the same as if no 1,2-dihalogen impurity were present. In some embodiments, "substantially removing a 1,2-dihalogen impurity" means that there may still be some 1,2-dihalogen impurity, so long as there is no measurable effect thereof.

As used herein, the term "about" is used to provide flexibility to a numerical range endpoint by providing that a given value may be "a little above" or "a little below" the endpoint.

As used herein, a plurality of items, structural elements, compositional elements, and/or materials may be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary.

Concentrations, amounts, and other numerical data may be expressed or presented herein in a range format. It is to be understood that such a range format is used merely for convenience and brevity and thus should be interpreted flexibly to include not only the numerical values explicitly recited as the limits of the range, but also to include all the individual numerical values or sub-ranges encompassed within that range as if each numerical value and sub-range is explicitly recited. As an illustration, a numerical range of "about 1 to about 5" should be interpreted to include not only the explicitly recited values of about 1 to about 5, but also include individual values and sub-ranges within the indicated range. Thus, included in this numerical range are individual values such as 2, 3, and 4 and sub-ranges such as from 1-3, from 2-4, and from 3-5, etc., as well as 1, 2, 3, 4, and 5, individually.

This same principle applies to ranges reciting only one numerical value as a minimum or a maximum. Furthermore, such an interpretation should apply regardless of the breadth of the range or the characteristics being described.

Compounds of the formula (II), including the compound of the formula (V), are useful precursors in the preparation of [$^{18}$F]-FACBC. In some embodiments, compounds of the formula (II) can be converted in a number of steps into other precursors in the synthesis of [$^{18}$F]-FACBC. Exemplary precursors that can be synthesized from compounds of the formula (II) include the compounds of the formula (V) and (VIII) shown in Scheme I, below.

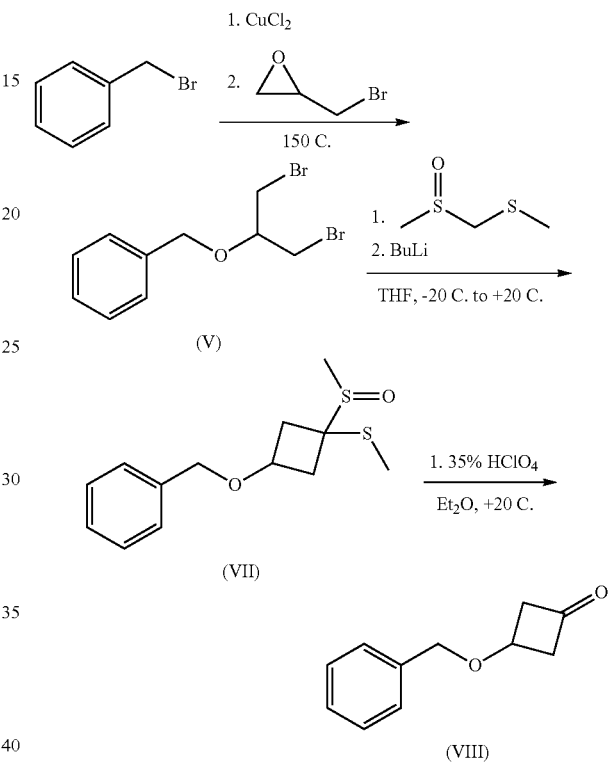

Although the synthetic procedure depicted in Scheme I uses specific reagents, those skilled in the art will recognize that other solvents and reagents may be used to achieve the desired transformations. For example, the reaction step that produces the compound of the formula (IV), though it is performed with CuCl$_2$, may also be performed using Hg$^{2+}$ (e.g., HgCl$_2$).

Each product shown in Scheme I may be purified by methods known in the art, including crystallization, chromatographic methods (e.g., HPLC, column chromatography, and the like), distillation, and the like.

The compound of formula (VIII) can be transformed into [$^{18}$F]-FACBC in a multi-step synthetic process, the final steps of which are shown below, in Scheme II.

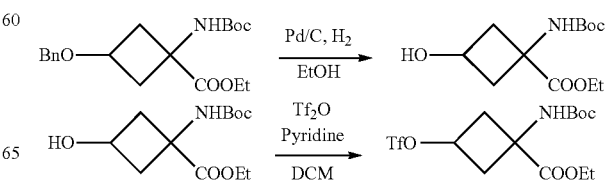

-continued

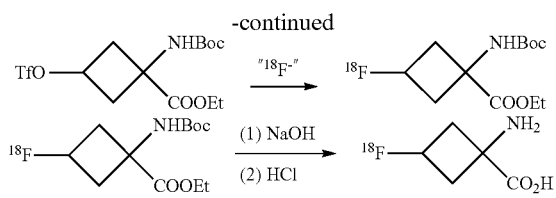

EXAMPLES

The following examples are provided to illustrate the present invention, and should not be construed as a limitation thereof.

Example 1

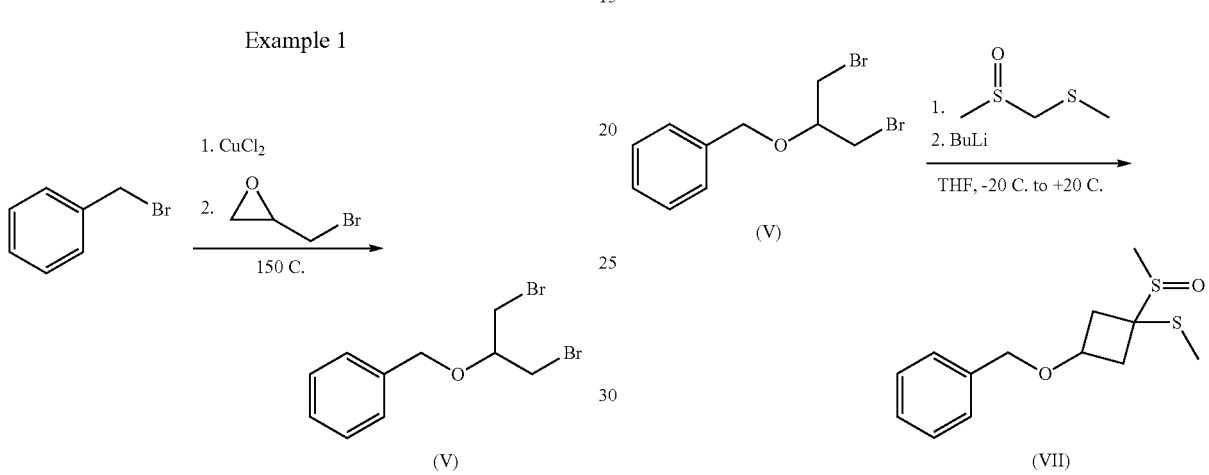

Copper (II) chloride (8.37 g) and benzyl bromide (750 mL) were stirred at room temperature with a magnetic stirrer bar. Epibromohydrin (674 mL) was added to the reaction. The reaction was heated to reflux (155-160° C.) for 11 hours before it was allowed to cool to room temperature. The reaction mixture was distilled under reduced pressure and the main fraction collected at 155-180° C. at 0.07-0.026 mbar. The reaction produced 1.5 kg of the correct compound in ~60% yield, with a purity of 70-75%.

Compound (V): $^1$H NMR (500 MHz, CDCl$_3$): $\delta_H$ 7.42-7.28 (m, 5H), 4.66 (s, 2H), 3.80 (quin, J=5.3 Hz, 1H), 3.57 (d, J=5.3 Hz, 4H).

The main impurity in the isolated product is the compound of the formula (IV). The compound of formula (IV) and the compound of formula (V) cannot be efficiently separated due to the similarities in boiling points of the two compounds. Typically 20 mol % of the compound of formula (IV) contaminates the desired product of formula (V).

The compound of formula (IV) is efficiently removed by treating the crude reaction mixture comprising the compound of formula (IV) and (V) with sodium methoxide. The crude compound of formula (V) (100 g) was charged into a reaction vessel (1 L), fitted with a nitrogen flow. Methanol (500 mL) was added to the vessel and stirred for 10-15 min. Sodium Methoxide (170 ml, 25% solution in methanol) was added to the reaction mixture. The reaction mixture was stirred for 4-6 h at room temperature. Completion of reaction monitored by HPLC.

The reaction mixture was quenched with water (300 mL). The methanol was evaporated under reduced pressure (e.g., on the rotary evaporator). The resulting residue was extracted into dichloromethane (DCM; 2×200 mL) and washed with water until the extract became neutral to litmus paper. The DCM was removed layer was separated and the DCM was removed under reduced pressure. The resulting residue was degassed to remove traces of DCM. The crude product was distilled under vacuum and the main fraction collected at 110-120° C. at 0.87-0.82 mbar.

Under these conditions, the compound of formula (IV) is converted into the compound of formula (VI). The resulting compound of the formula (VI) is a compound that has a sufficiently lower boiling point relative to the compound of formula (V), such that the compound of formula (VI) can be selectively removed by distillation.

Example 2

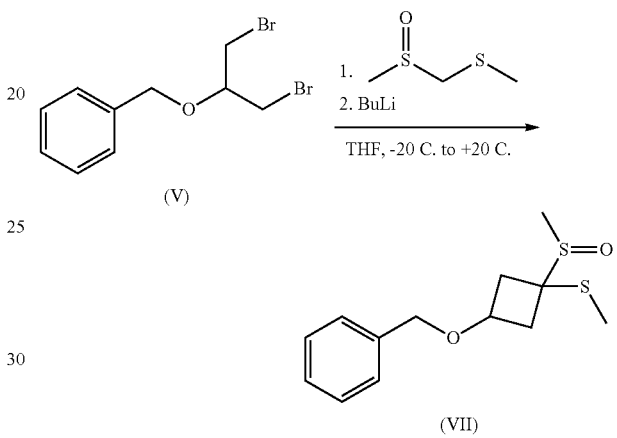

The inventors have surprisingly and unexpectedly found that the yield of this reaction may be increased by improving the quality of the starting material by, e.g., removing the compound of formula (IV) from the reaction mixture as described above.

The equipment was dried before use, and the atmosphere kept inert (nitrogen). Tetrahydrofuran (THF; 40 L) was charged to the reactor maintaining a temperature of about −20° C. The starting material methanesulfinyl-methylsulfanyl-methane (1.5 kg) was added, followed by the addition of n-BuLi (5.33 L, 2.5M in hexane) while maintaining a temperature below −8° C. After the n-BuLi addition the reaction was stirred for 2 hours at −10° C. The compound of formula (V) (1.86 kg) was pre-diluted in THF (5 L) and added to the reactor while maintaining the temperature below −10° C. The temperature was maintained at −10° C. for 1 hour before it was allowed to rise to room temperature overnight. The reaction was neutralized by adding acetic acid (~200 mL), followed by evaporation of THF. The raw product was then diluted with DCM (10 L) and washed with water (2×10 L). The organic phase was concentrated in vacuo, toluene (5 L) was added, and the crude product was azeotropically dried before separation. In some embodiments, the product is washed with cold hexanes (2 volumes) after the removal of the toluene.

Work up may be improved by replacing DCM with toluene during washing. While not being bound by theory, the toluene is believed to remove excess methanesulfinyl-methylsulfanyl-methane that may be left over from the reaction.

In some embodiments, this reaction may be conducted in toluene, thus eliminating the need to use and evaporate THF.

The raw product was diluted to 2 L with toluene and applied on to a silica gel pad. The pad was wet packed and pre-eluted with toluene. The pad used to separate a 1.5 kg batch was 40 cm in diameter and 22 cm high. After applying the raw product on to the pad it was eluted with 10 L fractions of eluents in the following order: 2×10 L toluene; 2×10 L toluene:dichloromethane (DCM) (50:50); 1×10 L DCM; 3×10 L DCM:ethylacetate (80:20); 5×10 L DCM:ethylacetate (70:30); 1×10 L DCM:ethylacetate (60:40); 5×10 L DCM:ethylacetate (50:50). The product fractions were collected and the solvent evaporated under vacuum. A total of 487 g of product was isolated. Side fractions containing 207 g of product were also isolated separately. The total yield of product when corrected for purity of the starting material is 56% (40% without the side fractions).

In some embodiments, the compound of formula (VII) may be distilled (e.g., high vacuum) instead of using column chromatography, as described above. In other embodiments, the compound of formula (VII) may be carried on to the next step (i.e., conversion to the compound of formula (VIII)) without purification.

Compound (VII): Diastereomer A: $^1$H NMR (500 MHz, CDCl$_3$): $\delta_H$ 7.38-7.27 (m, 5H), 4.47 (s, 2H), 4.35 (tt, J=7.4, 6.8 Hz, 1H), 2.79-2.73 (m, 1H), 2.71-2.66 (m, 1H), 2.47-2.40 (m, 1H), 2.18-2.13 (m, 1H), 2.45 (s, 3H), 2.12 (s, 3H). Diastereomer B: $^1$H NMR (500 MHz, CDCl$_3$): $\delta_H$ 7.38-7.27 (m, 5H), 4.46 (s, 2H), 4.20 (tt, J=7.5, 6.0 Hz, 1H), 3.10-2.99 (m, 2H), 2.60-2.55 (m, 1H), 2.38-2.32 (m, 1H), 2.55 (s, 3H), 2.13 (s, 3H).

Example 3

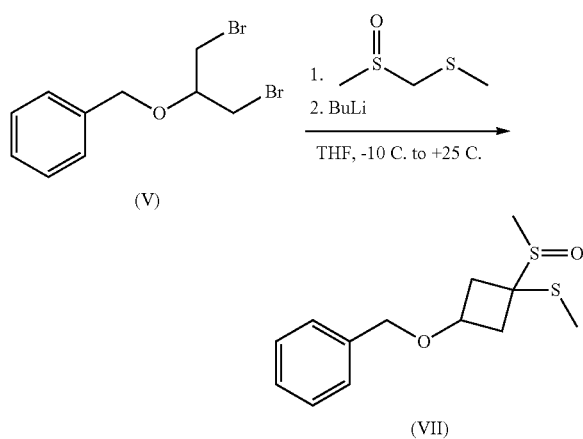

Dry THF (950 mL) was charged into a four necked reaction vessel (2 L) fitted with nitrogen flow. Methanesulfinyl-methylsulfanyl-methane (35 mL) was charged and the reaction mixture maintained at about −10° C. BuLi (140 mL) was added drop-wise to the reaction mixture, maintaining the temperature at −10° C. The reaction mixture was stirred for 1 hr. at −10° C. The compound of formula (V) (35 g), purified according to the methods described herein, was pre-diluted with THF (50 mL) was added, maintaining the temperature at −10° C. The temperature was maintained at −10° C. for 1 hr. before it was allowed to reach room temperature (approximately 25° C.). The reaction mixture was stirred at room temperature overnight (approximately 16 hrs).

The reaction mixture was neutralized with acetic acid and the THF was evaporated. The resulting residue was dissolved in toluene (600 mL) and washed with water (2×100 mL). The toluene layer containing the product can be taken as-is (i.e., without further purification) to the next step. See, e.g., Example 5.

Example 4

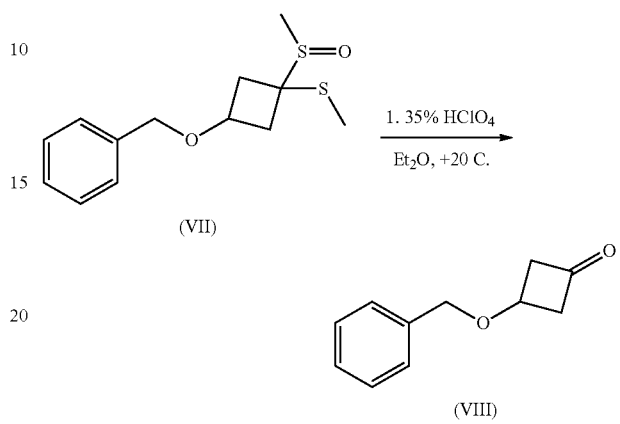

Diethyl ether (26.5 L) was added to the reactor (30-35 L reactor), and water cooling was applied on the reactor when additions started. The compound of the formula (VII) was added to the reactor (1.064 kg). Perchloric acid (0.932 L, 60%) was pre-diluted with water (0.664 L) and added slowly to the reactor at 10° C., over 20-30 minutes. After the addition of acid was complete, cooling was stopped, and the reaction was left to stir (vigorously) overnight at ~20° C. The reaction was quenched by the addition of NaHCO$_3$ (900 g) dissolved in 8 L water, until the pH was ~7. The water phase was discarded, and the reaction mixture was washed with an additional 7 L of water. The ether was removed in vacuo, toluene (2 L) was added, and the crude mixture was then azeotropically dried.

The raw product was diluted to ~2 L with toluene and loaded on to a silica gel pad. The pad was wet packed and pre-eluted with toluene. The pad used to separate a 1.5 kg batch was 40 cm in diameter and 22 cm high. After applying the raw product on to the pad it was eluted with 10 L fractions of eluents in the following order: 3×10 L toluene; 9×10 L toluene:ethyleacetate (95:5). The product fractions were collected and the solvent evaporated under vacuum. High vacuum was needed to remove the last 5% of toluene. A total of 533 g of product was isolated (yield=77%). Analysis by GC showed a purity of 95%.

Compound (VIII): $^1$H NMR (500 MHz, CDCl$_3$): $\delta_H$ 7.40-7.29 (m, 5H), 4.53 (s, 2H), 4.38 (tt, J=6.6, 4.7 Hz, 1H), 3.3-3.1 (m, 4H)

Example 5

In some embodiments, the diethylether used in the reaction described in Example 4 can be replaced with toluene. In other embodiments, the evaporation of the organic phase during workup can advantageously lead to the azeotropic removal of all water. In still other embodiments, when adding the bicarbonate to neutralize the reaction, the reactor can be stopped, the water phase can be removed prior to conducting the neutralization and washing procedure.

Crude compound of formula (VII) in toluene (600 mL) was charged into a four necked reaction vessel (2 L). The mixture was cooled to −15° C. A cold solution of perchloric acid (24 mL, pre-diluted with 24 mL of water) was added to the reaction mixture over a period of 30 minutes, maintaining the temperature below 10° C. The resulting mixture was allowed to reach room temperature over a period of 2 hrs. The reaction mixture was stirred overnight at 25° C. The reaction was quenched with solid NaHCO₃ (30 g) and adjusted the pH to ~7. The water phase was discarded and the reaction mixture washed with water (2×100 mL). Toluene was removed under reduced pressure (e.g., on the rotary evaporator). The crude product was distilled under vacuum and the main fraction collected at 86-92° C. at 0.87-0.82 mbar.

In some embodiments, the purification step (vacuum distillation) described in Example 2 can be left out. In other embodiments, toluene can be used as the solvent in Example 2 and the purification step can be eliminated, such that the compound of formula (VII) can be carried through, without purification, and transformed into the compound of formula (VIII). The compound of formula (VIII) can then be purified by distillation or by column chromatography.

While the foregoing description includes details and specific examples, it is to be understood that these have been included for purposes of explanation only, and are not to be interpreted as limitations of the present invention. Modifications to the embodiments described herein can be made without departing from the spirit and scope of the invention, which is intended to be encompassed by the following claims and their legal equivalents.

What is claimed is:

1. A method for substantially removing a 1,2-dihalogen impurity from a product mixture comprising:
   (a) reacting the product mixture with an alkoxide, thereby transforming the 1,2-dihalogen impurity into an alkene; and
   (b) removing the alkene.

2. The method of claim 1, wherein the alkoxide is methoxide.

3. The method of claim 1, wherein said methoxide is sodium methoxide.

4. The method of claim 1, wherein the alkene is removed by vacuum.

5. The method of claim 1, wherein the alkene is removed by vacuum distillation.

6. A method for substantially removing a 1,2-dihalogen impurity of the formula (I)

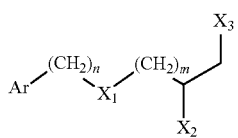

(I)

wherein:
Ar is a substituted or unsubstituted aryl or substituted or unsubstituted heteroaryl group;
$X_1$ is a heteroatom;
$X_2$ and $X_3$ are, independently the same or different, halogen; and
m and n are, independently the same or different, an integer from 1 to 5;
from a product mixture comprising a compound of the formula (II)

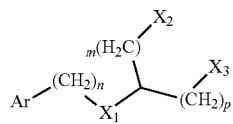

(II)

wherein Ar, $X_1$, $X_2$, $X_3$, n, and m are as defined above and p is an integer from 1 to 5;
wherein the method comprises:
   (a) reacting the product mixture with an alkoxide, thereby transforming the 1,2-dihalogen impurity of the formula (I) into an alkene of the formula (III)

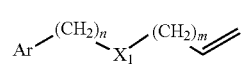

(III)

wherein Ar, $X_1$, n, and m are as defined above; and
   (b) removing the alkene of formula (III).

7. The method of claim 6, wherein the alkoxide is methoxide.

8. The method of claim 6, wherein said methoxide is sodium methoxide.

9. The method of claim 6, wherein the alkene of formula (III) is removed by vacuum.

10. The method of claim 6, wherein the alkene of formula (III) is removed by vacuum distillation.

11. The method of claim 6, wherein m and n in the compound of formula (I) are 1.

12. The method of claim 6, wherein m and n in the compound of formula (II) are 1.

13. The method of claim 6, wherein m and n in the compound of formula (III) are 1.

14. The method of claim 11, wherein $X_1$ is oxygen.

15. The method of claim 11, wherein $X_2$ and/or $X_3$ are bromine.

16. The method of claim 11, wherein Ar is phenyl.

17. The method of claim 11, wherein the compound of formula (I) is a compound of the formula (IV):

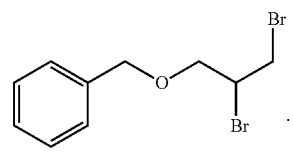

(IV)

18. The method of claim 12, wherein the compound of formula (II) is a compound of the formula (V):

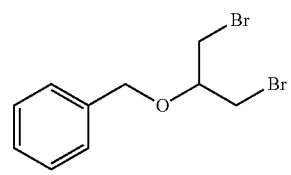

(V)

19. The method of claim 13, wherein the compound of formula (III) is a compound of the formula (VI):

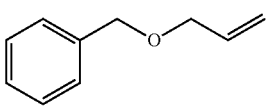
(VI)

20. A method of making a compound of the formula (VIII):

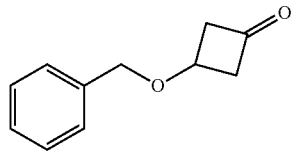 [SMILES: O=C1CC(OCc2ccccc2)C1]

the method comprising:
(a) reacting benzyl bromide with epibromohydrin to give a product mixture comprising a compound of the formula (IV) and a compound of the formula (V):

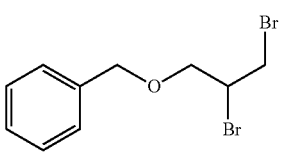
(IV)

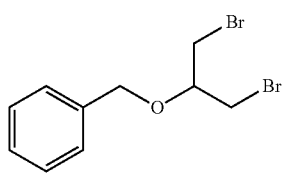
(V)

(b) reacting the product mixture with an alkoxide, thereby transforming the compound of formula (IV) into a compound of the formula (VI):

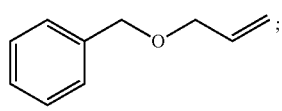
(VI)

(c) removing the compound of formula (VI) such that the compound of formula (V) remains;
(d) reacting the remaining compound of formula (V) with methanesulfinyl-methylsulfanyl-methane to give a compound of the formula (VII):

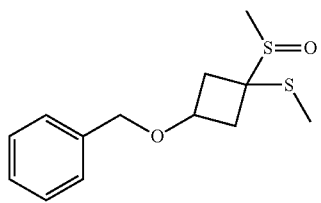
(VII)

and performing a work-up of the reaction with toluene;
(e) hydrolyzing the compound of formula (VII) in toluene to give a compound of the formula (VIII); and
(f) purifying the compound of formula (VIII).

21. The method of claim 20, wherein said purifying comprises vacuum distillation.

* * * * *